(12) United States Patent
Chen et al.

(10) Patent No.: US 10,100,550 B2
(45) Date of Patent: Oct. 16, 2018

(54) FOLDABLE TUBULAR ELEMENT WITH ONE RIGID DEGREE OF FREEDOM

(71) Applicant: Tianjin University, Tianjin (CN)

(72) Inventors: Yan Chen, Tianjin (CN); Sicong Liu, Tianjin (CN); Jianmin Li, Tianjin (CN); Kunfeng Wang, Tianjin (CN); Weilin Lv, Tianjin (CN); Kaori Shigetomi, Tianjin (CN)

(73) Assignee: Tianjin University, Tianjin (CN)

( * ) Notice: Subject to any disclaimer, the term of this patent is extended or adjusted under 35 U.S.C. 154(b) by 434 days.

(21) Appl. No.: 14/534,176

(22) Filed: Nov. 6, 2014

(65) Prior Publication Data

US 2016/0130796 A1 May 12, 2016
US 2017/0226730 A9 Aug. 10, 2017

Related U.S. Application Data

(63) Continuation-in-part of application No. PCT/CN2013/075521, filed on May 11, 2013.

(30) Foreign Application Priority Data

Dec. 5, 2012 (CN) .......................... 2012 1 0528507

(51) Int. Cl.
*E04B 1/343* (2006.01)
*A61F 2/844* (2013.01)
(Continued)

(52) U.S. Cl.
CPC ............. *E04H 15/32* (2013.01); *A61F 2/844* (2013.01); *B64G 9/00* (2013.01); *E04B 1/34357* (2013.01);
(Continued)

(58) Field of Classification Search
CPC .................................. E04C 2/00; B64G 1/00
See application file for complete search history.

(56) References Cited

U.S. PATENT DOCUMENTS

| 3,524,288 A | 8/1970 | Coppa |
| 4,359,842 A | 11/1982 | Hooker |

(Continued)

FOREIGN PATENT DOCUMENTS

| CN | 101926698 A | 12/2010 | |
| CN | 103015531 A * | 4/2013 | ......... E04B 1/34357 |
| CN | 203008123 U * | 6/2013 | ............. E04B 1/343 |

OTHER PUBLICATIONS

Tachi, T.; "One-DOF Cylindrical Deployable Structures with Rigid Quadrilateral Panels". Proceedings of the IASS Symposium 2009 (Sep. 28-Oct. 2, 2009).*

(Continued)

*Primary Examiner* — David Sample
*Assistant Examiner* — Donald M Flores, Jr.
(74) *Attorney, Agent, or Firm* — George G. Wang; Bei & Ocean

(57) ABSTRACT

Foldable tubular construct/element with one rigid degree of freedom is of a tubular construction formed by a number of single layered annular units which are connected in sequence; each single layered annular unit is of a prism having N ridge lines; two adjacent prisms each having N sides are connected to each other by sharing a polygon with N sides formed on an intersection plane; each prism with N ridge lines is composed of N rigid planar quadrilateral facets; two adjacent single layered annular units comprise N spherical mechanisms formed by the intersections of only four planar quadrilateral facets at each apex, where N is a number greater than 3.

4 Claims, 26 Drawing Sheets

(51) Int. Cl.
*E04H 15/32* (2006.01)
*E04C 2/40* (2006.01)
*E04C 2/42* (2006.01)
*B64G 99/00* (2009.01)
*A01G 9/00* (2018.01)
*A63H 33/16* (2006.01)
*E04B 1/32* (2006.01)
*E04B 7/10* (2006.01)
*E04C 2/30* (2006.01)
*E04H 15/52* (2006.01)

(52) U.S. Cl.
CPC ............... *E04C 2/40* (2013.01); *E04C 2/427* (2013.01); *A01G 9/00* (2013.01); *A63H 33/16* (2013.01); *E04B 1/32* (2013.01); *E04B 1/343* (2013.01); *E04B 1/34378* (2013.01); *E04B 7/10* (2013.01); *E04B 7/107* (2013.01); *E04B 2001/327* (2013.01); *E04B 2001/3247* (2013.01); *E04B 2001/3294* (2013.01); *E04C 2/30* (2013.01); *E04C 2/42* (2013.01); *E04H 15/52* (2013.01); *H05K 999/99* (2013.01); *Y10S 52/10* (2013.01); *Y10T 428/24686* (2015.01)

(56) References Cited

U.S. PATENT DOCUMENTS 6,233,880 B1    5/2001  Sogame et al.
2001/0035203 A1* 11/2001 Clee ........................ A01G 9/16
                                                    135/87

OTHER PUBLICATIONS

Tachi, T.; Miura, K.; "Rigid-Foldable Cylinders and Cells". J. IASS, vol. 53 (2012) No. 4 December n. 174, p. 217-226.*
Shigetomi et al. (CN 103015531 A)—(Apr. 3, 2013) (Google Patents—Machine Translation [to English]).*
"What is a Parallelogram?"; VirtualNerd; (Dec. 2017); <http://virtualnerd.com/geometry/quadrilaterals/properties-parallelograms/parallelogram-definition>.*
"Properties of Parallelograms"; Math Planet; (Dec. 2017); <https://www.mathplanet.com/education/geometry/quadrilaterals/properties-of-parallelograms>.*
Weisstein, Eric W. "Parallelogram." MathWorld—A Wolfram Web Resource (Dec. 2017); <http://mathworld.wolfram.com/Parallelogram.html>.*

* cited by examiner

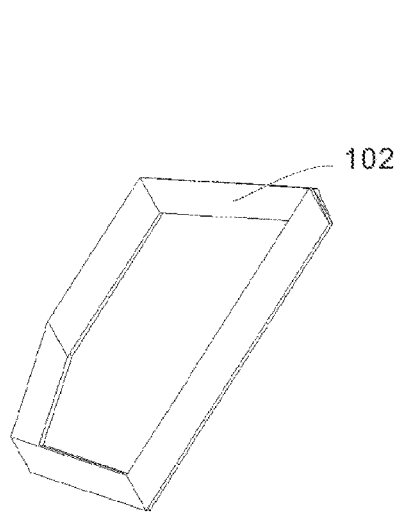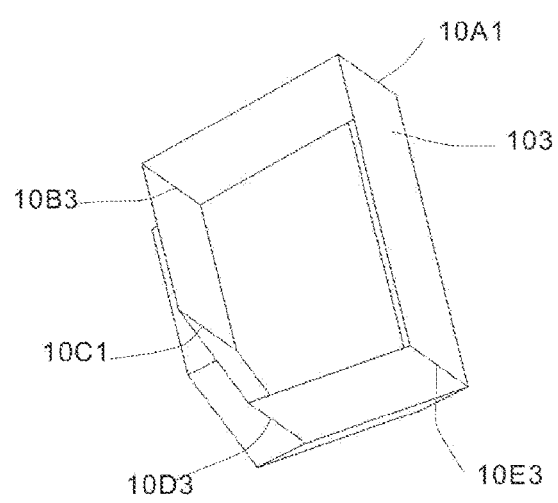
FIG. 47  FIG. 48
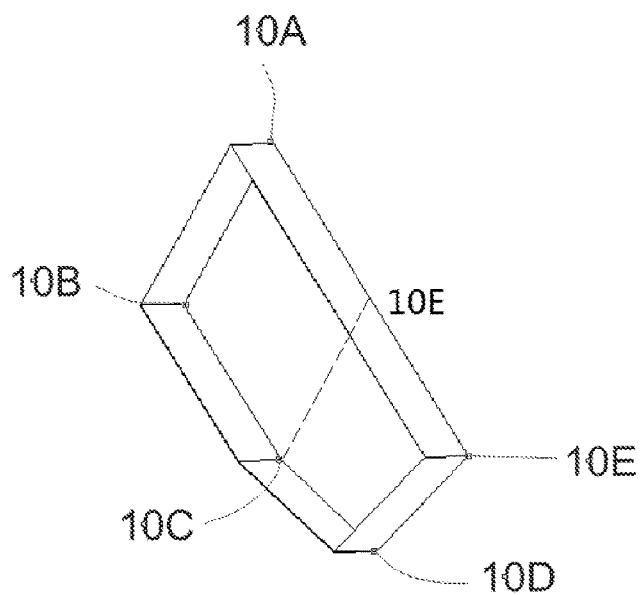
FIG. 49

FOLDABLE TUBULAR ELEMENT WITH ONE RIGID DEGREE OF FREEDOM

CROSS-REFERENCE TO RELATED APPLICATIONS

This is a CIP application based on PCT Application No. PCT/CN2013/075521, filed May 11, 2013, which claims priority from CN Application No. 201210528507.5, filed Dec. 5, 2012. The contents of the prior applications are incorporated herein in the entirety by reference.

FIELD OF THE INVENTION

The present invention relates to a foldable construction and more particularly, relates to a foldable tubular element with one rigid degree of freedom.

BACKGROUND OF THE INVENTION

An expandable and foldable tubular element composed of a number of planar units has various uses. For example, it may be used as a huge construction of space station, construction of moon base, used as support for human body blood vessel or digestive tract, or used as large or intermediate temporary residences after occurrence of serious natural disaster. When expanded, this kind of tubular element will define a space with certain volume. Also, it can be reduced to its smallest size by folding, thus bringing convenience in storage and transportation. In recent years, types of foldable tubular elements have been proposed by Hoberman in U.S. Pat. No. 4,780,344, U.S. Pat. No. 4,981,732 and U.S. Pat. No. 5,234,727, Guest and Pellegrino jointly, Sogame in U.S. Pat. No. 6,233,880B1, and proposed by Furuya and Nojima and so on. These are capable of folding and expanding as described above. These kinds of elements however fold and expand based on wide elastic and plastic deformation of materials used. It is hard to accurately control the process of folding and expanding and this imposes limitation on their application. Moreover, as deformation of the constitutional units of the element results in entire deformation of the element and accordingly, the current tubular foldable elements are generally used as a disposable products.

SUMMARY OF THE INVENTIONS

The object of the invention is to overcome drawbacks of the prior art and also provide a foldable tubular element with one rigid degree of freedom capable of accurately controlling folding and expanding process of the element, reducing complexity of folding and expanding the element, and being capable of repeated used.

According to the present invention, a foldable tubular element with one rigid degree of freedom is of a tubular construction formed by a number of single layered annular units which are connected in sequence. Each single layered annular unit is of a prism having N sides. Two adjacent prisms each having N sides are connected to each other by sharing a polygon with N sides formed on an intersection plane defined by connection of a first and a final ridge lines. Each prism with N sides is composed of N rigid planar quadrilateral facets. Two adjacent single layered annular units comprise N spherical mechanisms formed by intersection of only four planar quadrilateral facets around an apex. The polygon having N sides formed in the intersection plane of the two adjacent single layered annular units is a planar polygon with arbitrary sides in addition to triangle. The ridge lines of each prism having N sides are parallel to each other. When N is an even number, and the N-side polygon formed in the intersection plane of the two adjacent single layered annular units is a line-symmetric N-side polygon having at least one diagonal symmetric axis, the first and final ridge lines of the tubular element are in the same plane, and the plane in which the first and final ridge lines of the tubular element are located is perpendicular to one diagonal symmetric axis of the N-side polygon. Here, N is an integer larger than 3.

As one aspect of the present invention, there is provided a foldable tubular construct/device/element with one rigid degree of freedom, comprising a plurality of layered tubular units each with an enclosing side wall, a head rim and tail rim, said enclosing side wall being formed by n side faces, said head rim and said tail rim each defining an n-sided polygon, said side faces each being a rigid planar quadrilateral with two opposing sides forming two side jointing lines with corresponding sides of two adjacent faces of a same tubular unit and another side forming a base joining line with a corresponding side of an adjacent face of a different tubular unit, said plurality of layered tubular units being joined sequentially wherein a head-to-head connection is formed between the head rim of a tubular unit and the head rim of a preceding adjacent tubular unit and/or a tail-to-tail connection is formed between the tail rim of said tubular unit and the tail rim of a following adjacent tubular unit; each of said tubular unit has exactly n side joining lines, all parallel to each other; said head-to-head connection or tail-to-tail connection consists of n base joining lines interconnected to form an n-sided polygon within a same plane; two side joining lines and two base joining lines join at one end to form an apex; exactly n apexes are formed in each head-to-head connection or tail-to-tail connection; and n is a number greater than 3.

The device of the invention has the following advantages.

The foldable tubular element of the invention is constructed of planar units to which no deformation will occur and a rotation pair formed by connection lines of two adjacent planar units. Accurate control may be done to the folding and expanding process of the element. Furthermore, as the tubular element of the invention only has one rigid degree of freedom, complexity in folding and expanding of the element is further reduced. Therefore, the present element is more reliable than a prior art element and may be reused.

The tubular element of the invention may be designed using a simple method and, may be assembled conveniently. As the entire element can be folded into a compact arrangement, storage and transportation of the same is also facilitated. In addition, the tubular element of the invention is not intended to be limited to one with specific shape or size. It may also meet different requirements with different purposes.

BRIEF DESCRIPTION OF THE DRAWINGS

FIG. 47 shows a fully folded foldable tubular element of FIG. 46;

FIG. 48 shows structure of two adjacent layered annular members forming the foldable tubular element of FIG. 46;

FIG. 49 shows a top plan view of the annular members of FIG. 46;

In above figures:

Figure 1:
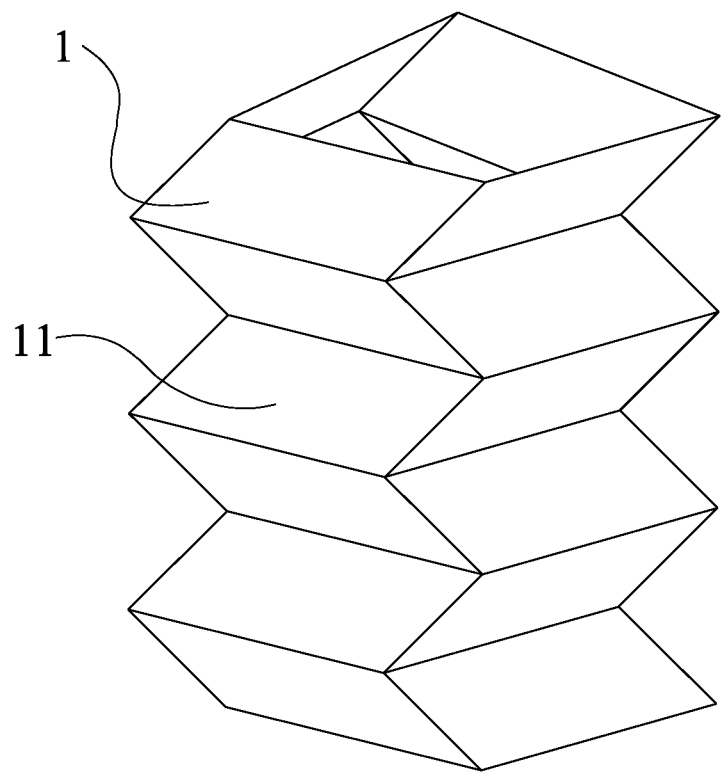
FIG. 1 shows a first embodiment of a foldable tubular element with one rigid degree of freedom according to the invention, illustrating a foldable tubular element being expanded and composed of a quadrangular prism single layered unit in which an intersection line between two adjacent layers form a line-symmetric rectangular (that is kite shape) with a symmetric axis.

Reference numeral 1 represents a foldable tubular element composed of plural quadrangular prism single layer units, wherein the intersection line between two adjacent layers forms a line-symmetric rectangular with a symmetric axis;

Reference numeral 2 represents a foldable tubular element composed of quadrangular prism single layer units, wherein the intersection line between two adjacent layers forms a rotational symmetric rectangular;

Reference numeral 3 represents a foldable tubular element composed of hexagon prism single layer units, wherein the intersection line between two adjacent layers forms a line-symmetric hexagon with a symmetric axis;

Reference numeral 4 represents a foldable tubular element composed of hexagon prism single layer units, wherein the intersection line between two adjacent layers forms a rotational symmetric hexagon;

Reference numeral 5 represents a foldable tubular element composed of octagonal prism single layer units, wherein the intersection line between two adjacent layers forms a line-symmetric octagon with a symmetric axis;

Reference numeral 6 represents a foldable tubular element composed of octagonal prism single layer units, wherein the intersection line between two adjacent layers forms a rotational symmetric octagon;

Reference number 7 denotes a foldable tubular element made of a plurality of single layered units with the same intersection angle;

Reference numeral 8 represents a foldable tubular element composed of hexagonal prism single layer units, wherein the intersection line between two adjacent layers forms an asymmetric hexagon;

Reference numeral 9 represents a foldable tubular element composed of octagonal prism single layer units, wherein the intersection line between two adjacent layers forms an asymmetric octagon;

Reference numeral 10 represents a foldable tubular element composed of pentagon prism single layer units, wherein the intersection line between two adjacent layers forms an asymmetric pentagon;

Reference numeral 11 represents a foldable tubular element composed of a polygon with seven sides prism single layer units, wherein the intersection line between two adjacent layers forms an asymmetric polygon with seven sides;

Reference numeral 12 represents a foldable tubular element composed of a random single layer units;

Reference numeral 13 represents an example structure of the foldable tubular element which is composed of hexagonal prism single layer units;

Reference number i1 represents expanded status of the structure i (i=1, 2, 3, 4, 5, 6, 7, 8, 9);

Reference number i2 represents fully folded status of the structure i (i=1, 2, 3, 4, 5, 6, 7, 8, 9);

Reference number i3 represents an annular structure composed of the two adjacent layered annular members of the structure i (i=1, 2, 3, 4, 5, 6, 7)

Reference number i4 represents the annular structure i3 in concavely folded status (i=1, 3);

Reference number i5 represents the concavely folded annular structure i in an expanded status (i=1, 3);

Reference number i6 represents the concavely folded annular structure i in a folded status (i=1, 3);

Reference number iX represents intersection points of four planar units of the structure i and the center of the spherical mechanism, and also represents apex of two adjacent layers of intersection lines of the annular structure (X=A, B, C, D, E, F, G, H);

Reference number iX' represents a virtual apex which does not actually exist;

Reference number iXj represents an intersection line j passing through the apex X of the structure i, and also represents a side line between two adjacent layers of intersection lines (j=1, 2, 3, 4); when seen from outside of the tubular element, the four intersection lines are numbered counterclockwise about the apex iX; and Reference number iXj(j+1) represents an angle between two intersection lines j and j+1 which are crossed at the apex X of the structure i;

DETAILED DESCRIPTION OF PARTICULAR EMBODIMENTS OF THE INVENTION

The present invention will be described below in conjunction with drawings and embodiments.

A foldable tubular element with one rigid degree of freedom according to the invention is of a tubular construction formed by a number of single layered annular units which are connected in sequence. Each single layered annular unit is of a prism having N sides. Two adjacent prisms each having N sides are connected to each other by sharing a polygon with N sides formed on an intersection plane defined by connection of a first and a final ridge lines. Each prism with N sides is composed of N rigid planar quadrilateral facets. Two adjacent single layered annular units comprise N spherical mechanisms formed by intersection of only four planar quadrilateral facets around an apex. The polygon having N sides formed in the intersection plane of the two adjacent single layered annular units is a planar polygon with arbitrary sides in addition to triangle. When N is an even number, and the N-sided polygon formed in the intersection plane of the two adjacent single layered annular units is a line-symmetric N-side polygon having at least one diagonal symmetric axis, the first and final ridge lines of the tubular element are in the same plane, and the plane in which the first and final ridge lines of the tubular element are located is perpendicular to one diagonal symmetric axis of the N-side polygon. Here, N is an integer larger than 3.

The tubular element may be of a straight tubular element. The planar quadrangular unit is of a parallelogram. The straight tubular element includes a polygon having N sides formed in the intersection plane of the two adjacent single layered annular units, which may be a planar polygon with arbitrary sides greater in number than that of a triangle.

The tubular element may be of a bent tubular element with a zig-zag axis. The planar quadrangular units of the bent tubular element are all or partially of trapezoid.

In the structure of the invention, the intersection lines of two adjacent planar quadrangular units work as a rotary central axis with a rotation pair. In addition, only four intersection lines intersect at a same apex equivalent to a spherical 4R mechanism with one rigid degree of freedom. The configuration in which only four planar quadrangular units intersect at a same apex ensures that the folding and expanding of two adjacent layered annular units will only have one rigid degree of freedom. This further ensures that the formed tubular element will also only have one rigid degree of freedom. At time the tubular element is axially expanded or folded, it also is expanded or folded in a radial direction. The full expansion of the tubular element occurs when a certain basic combination of the structure is fully expanded. The full folding of the tubular element occurs when the planar quadrangular unit contacts an adjacent unit.

The detailed description of the invention is provided below in conjunction to each drawing.

Figure 2:
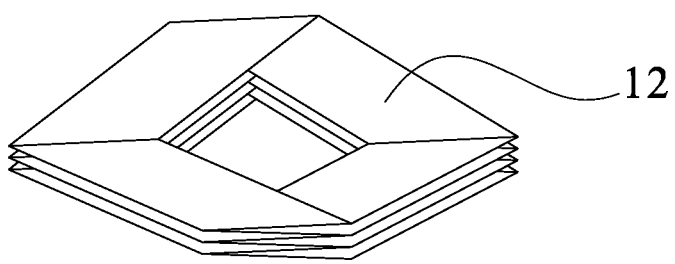
FIG. 2 shows the structure of the fully folded foldable tubular element of FIG. 1.
Figure 3:
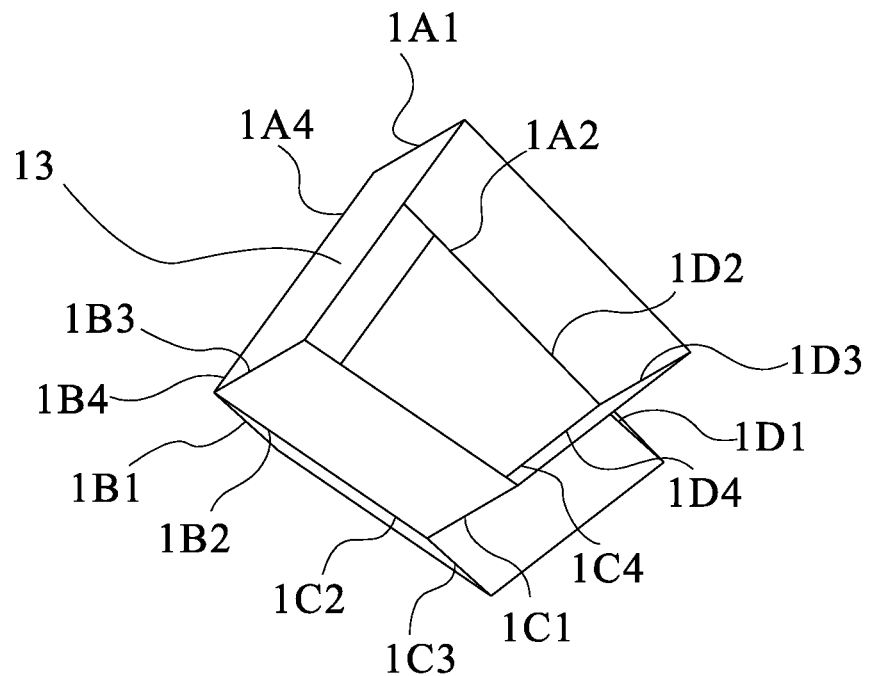
FIG. 3 shows the structure of two adjacent layered annular members of the foldable tubular element of FIG. 1.
Figure 4:
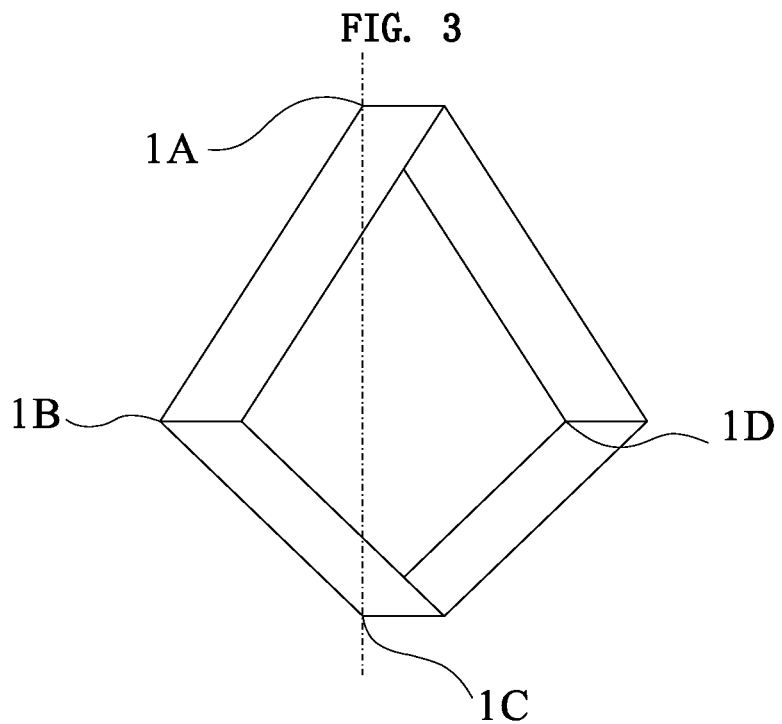
FIG. 4 shows a top plan view of the annular members of FIG. 3.

FIG. 1 shows a foldable tubular element with one rigid degree of freedom according to the invention, illustrating a foldable tubular element being expanded and composed of a quadrangular prism single layered unit in an expanded status 11; FIG. 2 shows the structure 1 in fully folded status 12; and FIG. 3 shows two adjacent single layered annular units 13 forming the structure of FIG. 1. The two single layered annular units of FIG. 3 are connected with each other by sharing intersection lines in a same plane by two quadrangular prisms. Each said quadrangular prism is constructed of four rigid parallelogram units. Adjacent two said single layered annular units include a spherical mechanism formed by intersection of only four planar rectangular units at an apex. The apexes include 1A, 1B, 1C and 1D. Two adjacent side single layered annular units form at an intersection plane a polygon for example a kite shape 1A1B1C1D with a symmetric axis as shown in FIG. 3. The symmetric axis shown in FIG. 4 overlaps the diagonal 1A1C.

Four ridge lines of each single layered quadrangular are parallel to each other. In other words, the ridge lines 1A1, 1B3, 1C1 and 1D3 are parallel to each other as shown in FIG. 3. Also, in addition to meeting parallel relationship, in each group, the first ridge line must be coplanar with the final ridge line, and this plane must be perpendicular to the symmetric axis 1A1C. For example, as shown in FIG. 3, planes 1A11A3 (1A3 is a ridge line of a single layer and is not denoted in this figure), 1B31B1, 1C11C3 and 1D31D1, in each of which two ridge lines locate, are all perpendicular to the symmetric axis 1A1C. In this figure, 1A2, 1A4, 1B4, 1B2, 1C2, 1C4 and 1D4 are ridge lines of two quadrangular prisms respectively and can be seen from the figure.

Figure 5:
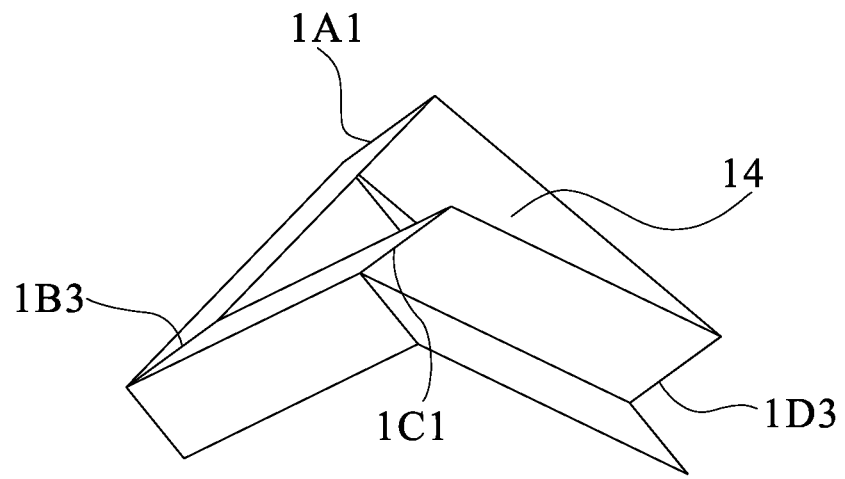
FIG. 5 shows a concavely folded state of the annular member of FIG. 3 where the intersection line between two adjacent layers has been changed from a convex kite shape to a concave kite shape.
Figure 6:
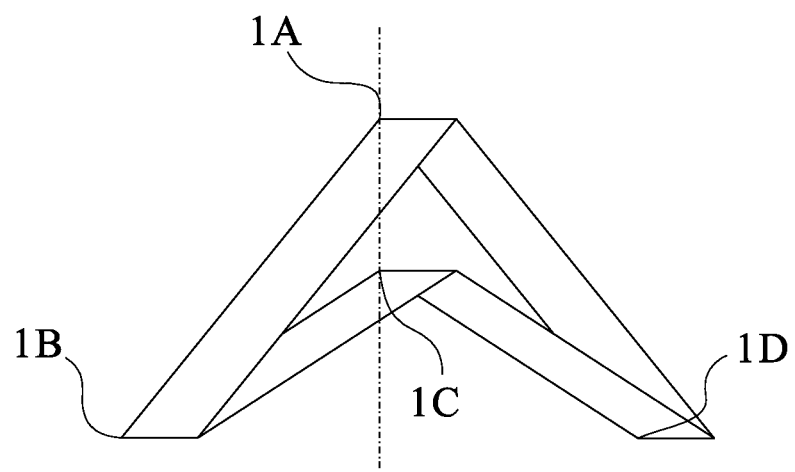
FIG. 6 shows a top plan view of the annular member of FIG. 5 in a concavely folded state.
Figure 7:
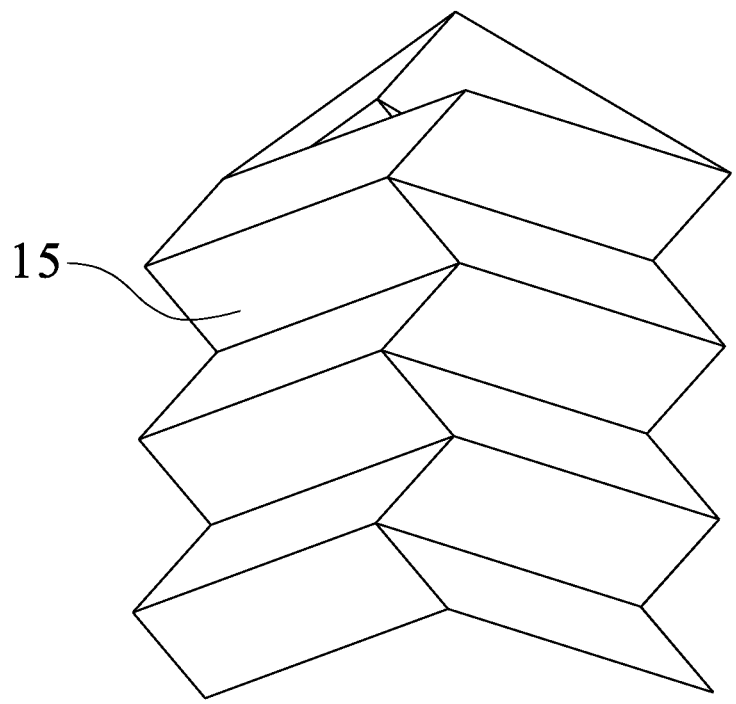
FIG. 7 shows the foldable tubular element of FIG. 1 in concavely folded state, and also shows the result after the annular members of FIG. 5 are connected together.
Figure 8:
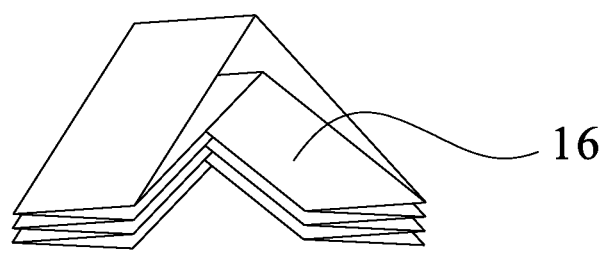
FIG. 8 shows a fully folded foldable tubular element of FIG. 7.

FIGS. 5 and 6 show an annular structure 14 which is formed by moving the apex 1C to the apes 1A of the annular structure 13 of FIG. 3. By expanding to a fully expanded status, the annular structure 13 converts to a folding status 14 having a concave kite-shaped cross section. FIGS. 7 and 8 shows expanded status 15 and fully folded status 16 of the foldable tubular element 1 in a concave folded status. Comparatively, the fully folded status 16 of FIG. 8 further reduces space occupied by the structure than does the fully folded status 12 of FIG. 2.

Figure 9:
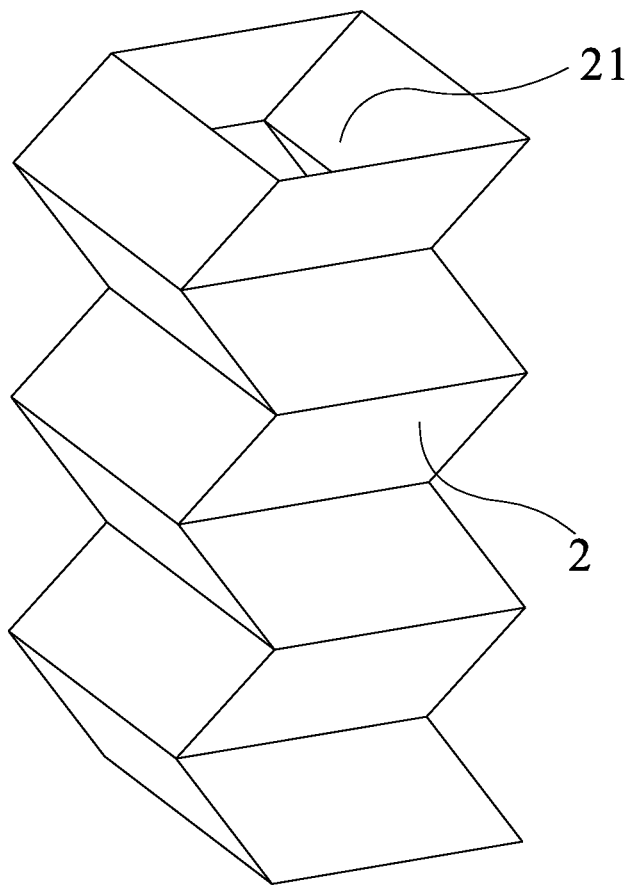
FIG. 9 shows a second embodiment of a foldable tubular element with one rigid degree of freedom according to the invention, illustrating a foldable tubular element being expanded, wherein an intersection line between two adjacent layers forms a rotational symmetric rectangle with a symmetric center located on the intersection of two orthogonal lines of the rectangle.
Figure 10:
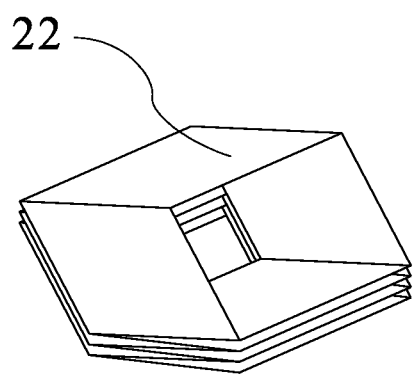
FIG. 10 shows a fully folded foldable tubular element of FIG. 9.
Figure 11:
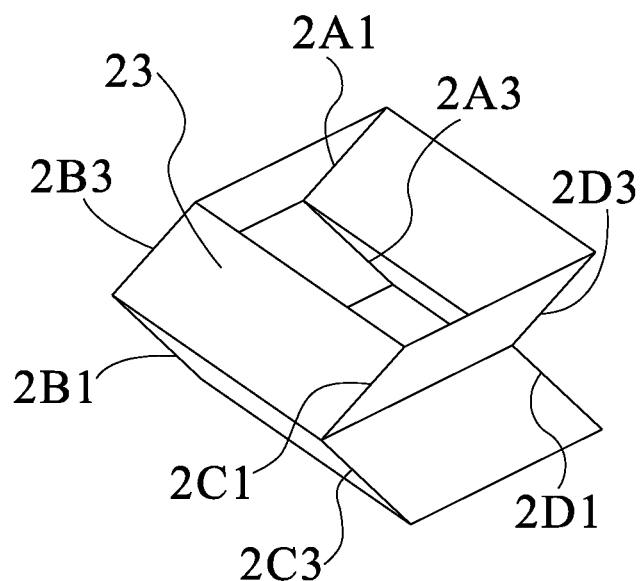
FIG. 11 shows a structure of two adjacent layered annular members forming the foldable tubular element of FIG. 9.
Figure 12:
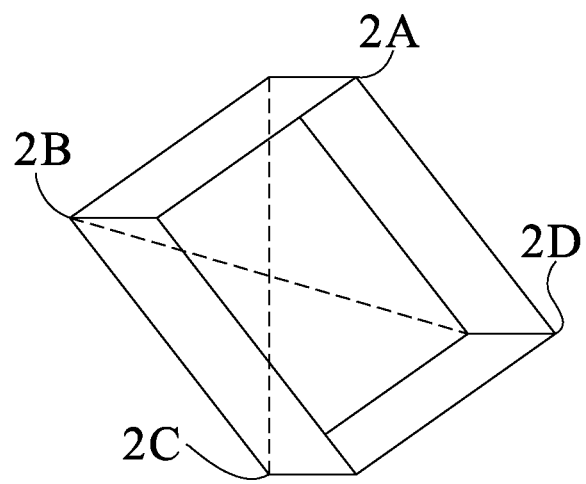
FIG. 12 shows a top plan view of the annular members of FIG. 11.

FIG. 9 shows a foldable tubular element 2 in an expanded status 21 and composed of a number of single layered quadrangular prisms. FIGS. 10, 11 and 12 respectively show the fully folded status 22 of the structure 2, an annular structure 23 and its top plan view. As shown in FIG. 11, in the same manner as the annular structure 13 of FIG. 3, the annular structures 23 are connected with each other by sharing intersection lines in the same plane as two adjacent quadrangular prisms. The ridge lines of each quadrangular prism are parallel to each other. As shown in this figure, ridge lines 2A1, 2B3, 2C1, 2D3 of the quadrangular prism of an upper layer are parallel to each other; and ridge lines 2A3, 2B1, 2C3, 2D1 of the quadrangular prism of a lower layer are also parallel to each other. The difference lies in that the intersection lines between two said quadrangular prisms are a rotationally symmetric rectangular 2A2B2C2D as shown in FIG. 12. The symmetric center of the rectangular is an intersection point of two diagonals 2A2C and 2B2D.

Figure 13:
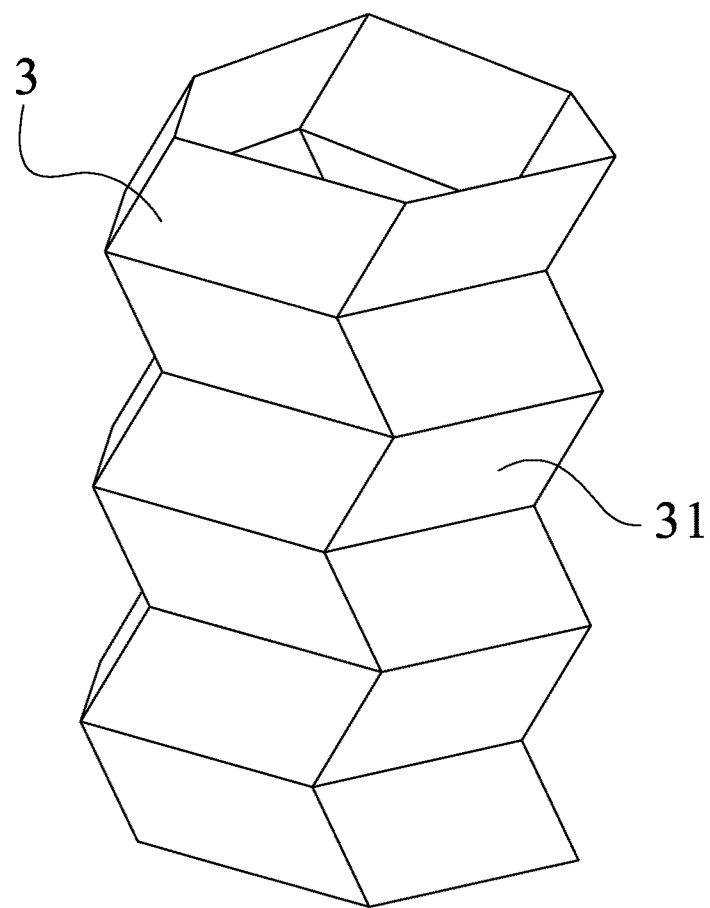
FIG. 13 shows a third embodiment of a foldable tubular element with one rigid degree of freedom according to the invention, illustrating a foldable tubular element being expanded and composed of a hexagonal prism single layered unit in which an intersection line between two adjacent layers forms a line-symmetric hexagon with a symmetric axis.
Figure 14:
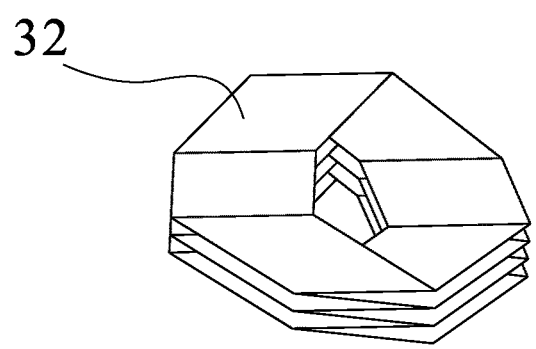
FIG. 14 shows a fully folded foldable tubular element of FIG. 13.
Figure 15:
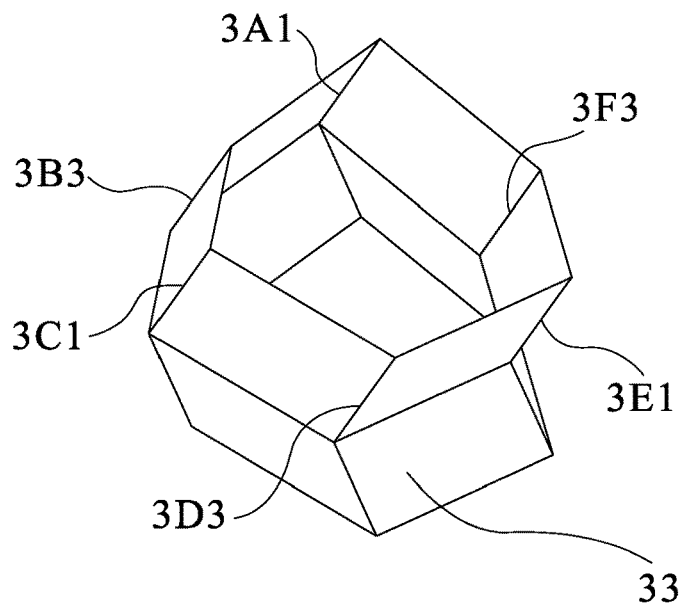
FIG. 15 shows the structure of two adjacent layered annular members forming the foldable tubular element of FIG. 13.
Figure 16:
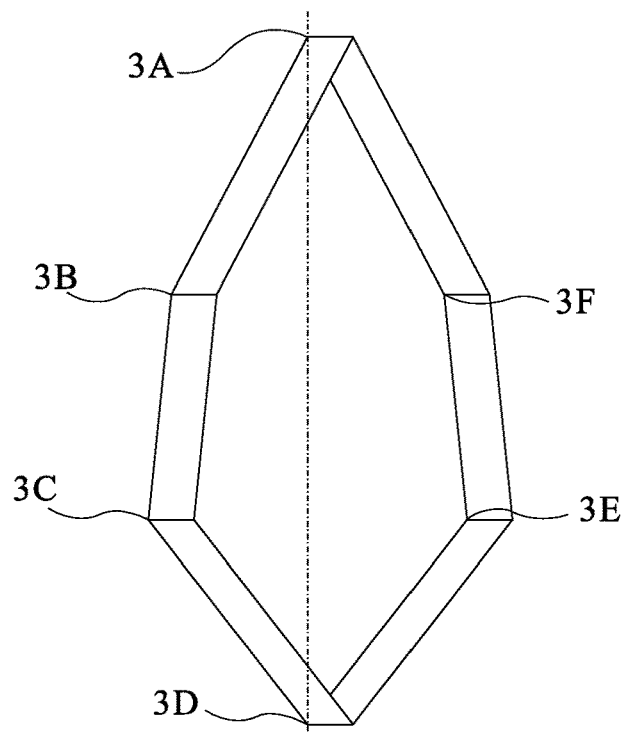
FIG. 16 shows a top plan view of the annular members of FIG. 15.

FIG. 13 shows a foldable tubular element 3 in an expanded status 31 and composed of a hexagonal prism single layered unit; FIGS. 14, 15 and 16 respectively show the fully folded status 32 of the structure 3, an annular structure 33 and its top plan view. As shown in FIG. 15, the annular structure 33 is formed by two adjacent hexagons connected with each other. The intersection lines between the two hexagons are a line-symmetric hexagon 3A3B3C3D3E3F with a symmetric axis running across the apexes 3A and 3D, as shown in FIG. 16. All ridge lines of each hexagon are parallel to one another. As shown in FIG. 15, the ridge lines 3A1, 3B3, 3C1, 3D3, 3E1 and 3F3 are parallel to each other. For the tubular element 31 shown in FIG. 13, in each group, the first ridge line and final ridge line are located in a same plane perpendicular to the symmetric axis 3A3D of the intersection lines of the adjacent hexagons.

Figure 17:
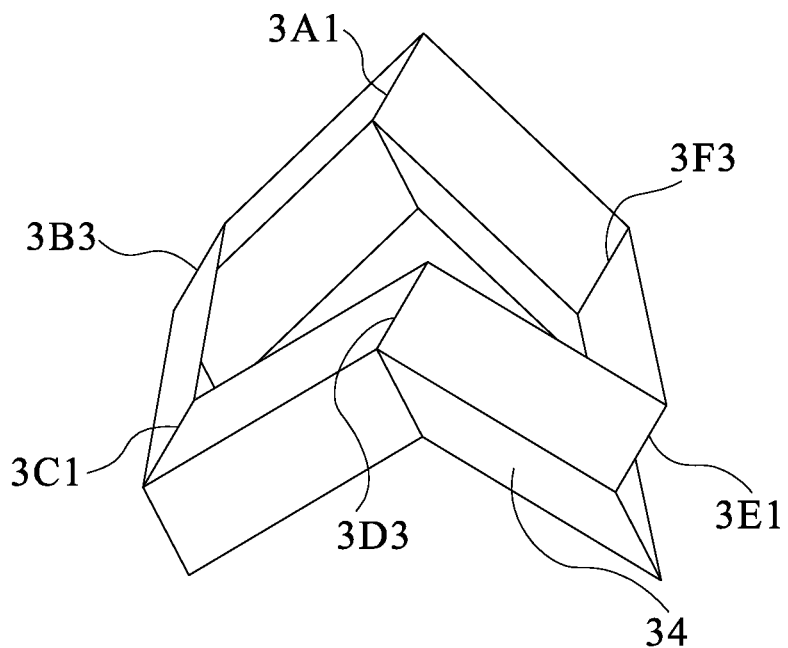
FIG. 17 shows the concavely folded state of the annular member of FIG. 15 where the intersection line between two adjacent layers has been changed to a concave hexagon from a convex hexagon.
Figure 18:
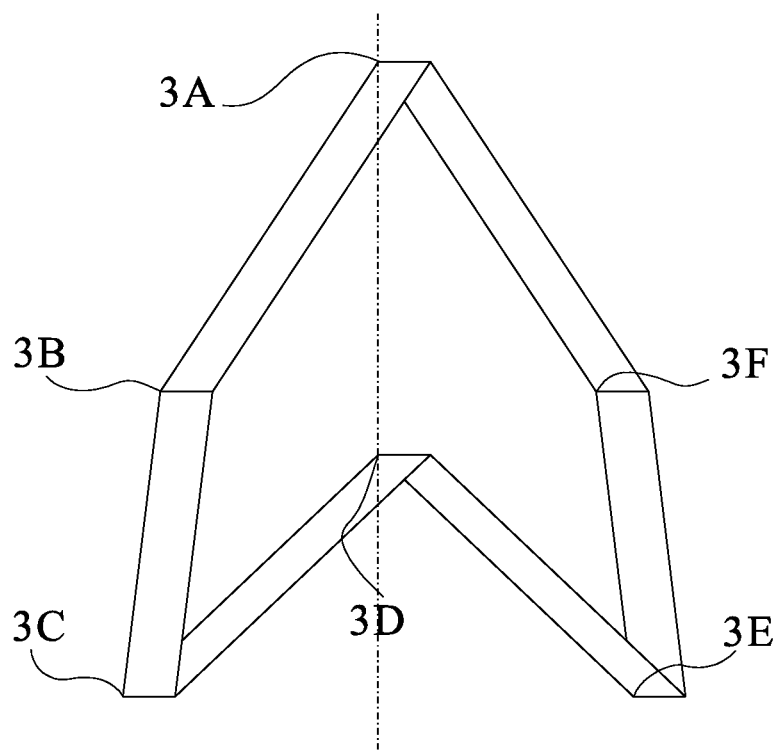
FIG. 18 shows a top plan view of the annular member of FIG. 17.
Figure 19:
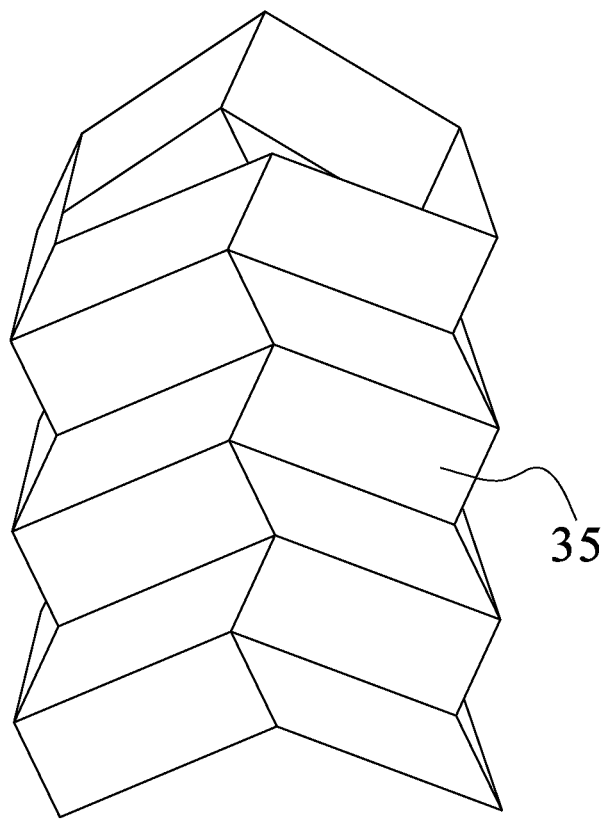
FIG. 19 shows the foldable tubular element of FIG. 13 in a concavely folded state, and also shows the result after the annular members of FIG. 17 are connected together.
Figure 20:
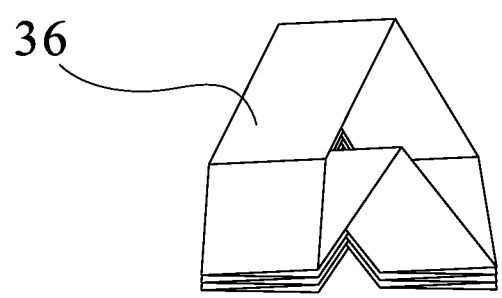
FIG. 20 shows a fully folded foldable tubular element of FIG. 19.

FIG. 17 shows the annular structure 33 of FIG. 15 in a concavely folded status 34. FIGS. 18, 19 and 20 respectively show top plan view of the annular structure 34, the tubular element made of the annular structure 34 in an expanded status 35 and fully folded status 36.

Figure 21:
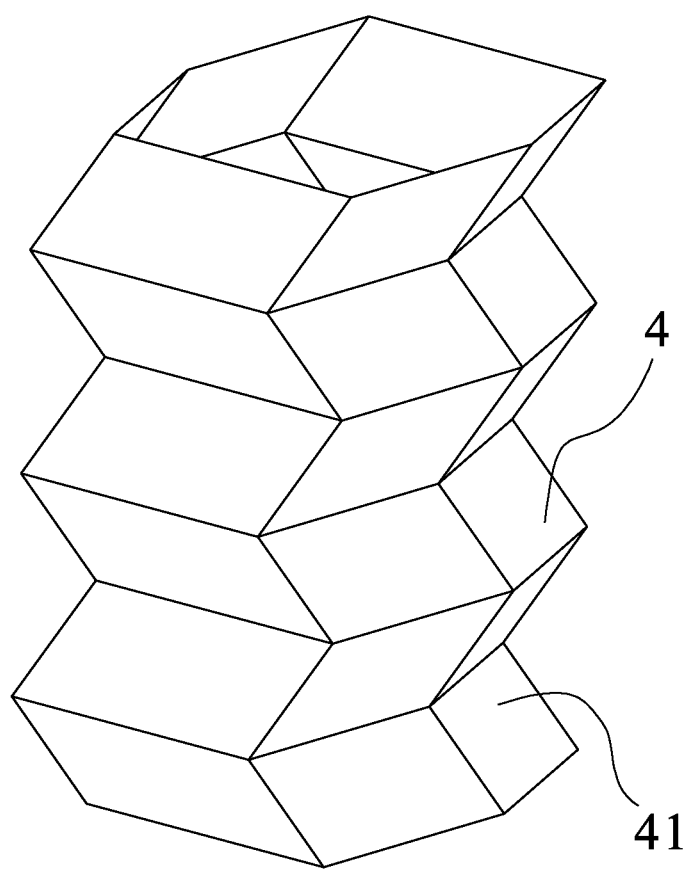
FIG. 21 shows a fourth embodiment of a foldable tubular element with one rigid degree of freedom according to the invention, illustrating a foldable tubular element being expanded and composed of a hexagonal prism single layered unit in which an intersection line between two adjacent layers forms a rotationally symmetric hexagon with a symmetric axis located on the intersection point of the orthogonal lines of the hexagon.
Figure 22:
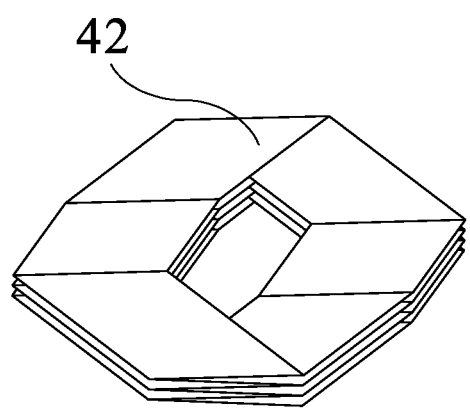
FIG. 22 shows a fully folded foldable tubular element of FIG. 21.
Figure 23:
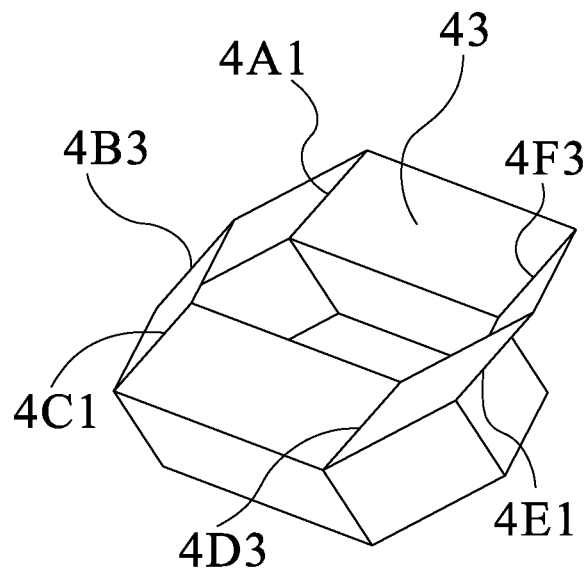
FIG. 23 shows the structure of the annular members forming the foldable tubular element of FIG. 21.
Figure 24:
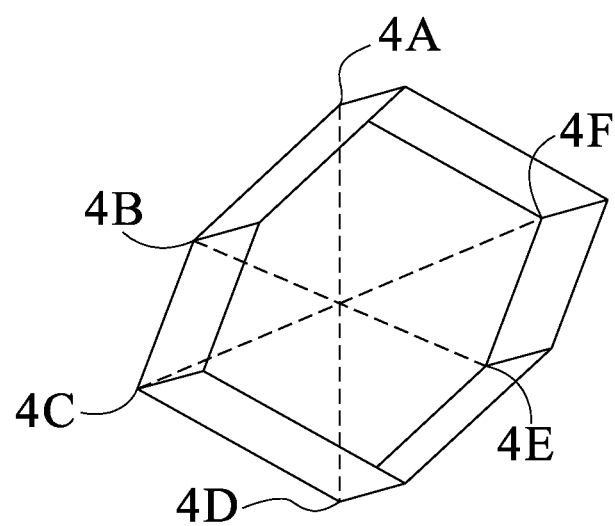
FIG. 24 shows a top plan view of the annular members of FIG. 23.
Figure 25:
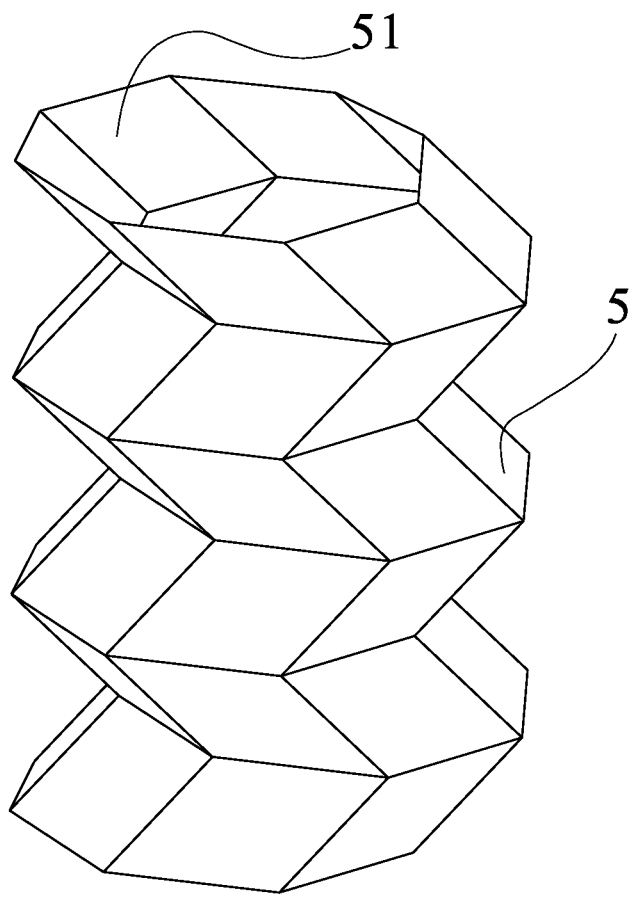
FIG. 25 shows a fifth embodiment of a foldable tubular element with one rigid degree of freedom according to the invention, illustrating a foldable tubular element being expanded and composed of an octagonal prism single layered unit in which an intersection line between two adjacent layers forms a line-symmetric octagon with a symmetric axis.
Figure 26:
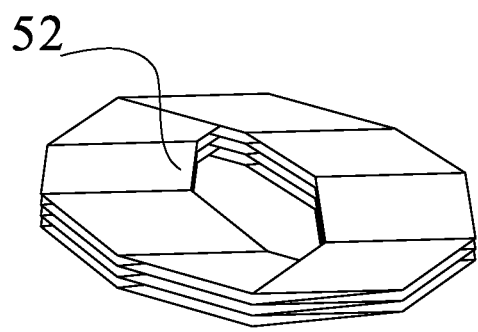
FIG. 26 shows a fully folded foldable tubular element of FIG. 25.

FIG. 21 shows a foldable tubular element 4 in an expanded status 41 and is composed of a hexagonal prism single layered unit. FIGS. 22, 23 and 24 respectively show the fully folded status 42 of the structure 4, an annular structure 43 forming the structure 4 and top plan view of the annular structure 43. Different from the structure 3, as shown in FIG. 23, the intersection lines of the adjacent hexagons constituting the annular structure 43 are a rotationally symmetric hexagon 4A4B4C4D4E4F. The symmetric center is an intersection line of the diagonals 4A4D, 4B4E and 4C4F, as shown in FIG. 24. The ridge lines 4A1, 4B3, 4C1, 4D3, 4E1 and 4F3 in the annular structure 43 are parallel to each other. Functionally, the structure 4 is also capable of being fully expanded, concavely or convexly folded.

Figure 27:
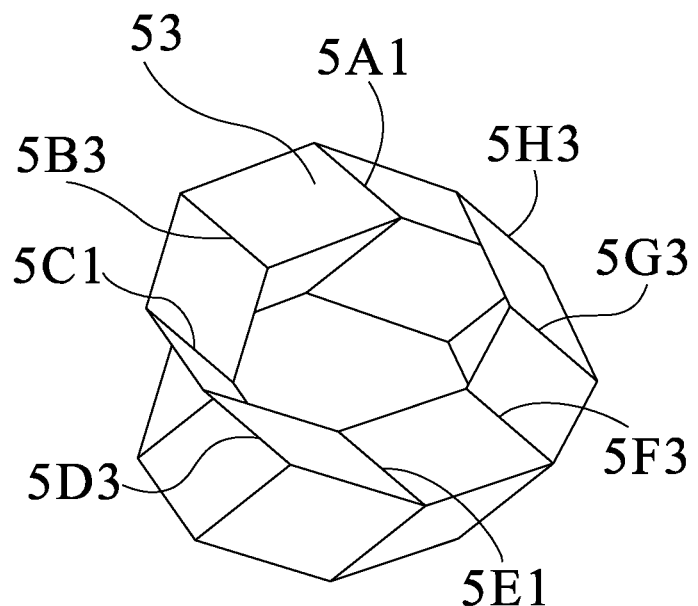
FIG. 27 shows structure of two adjacent layered annular members forming the foldable tubular element of FIG. 25.
Figure 28:
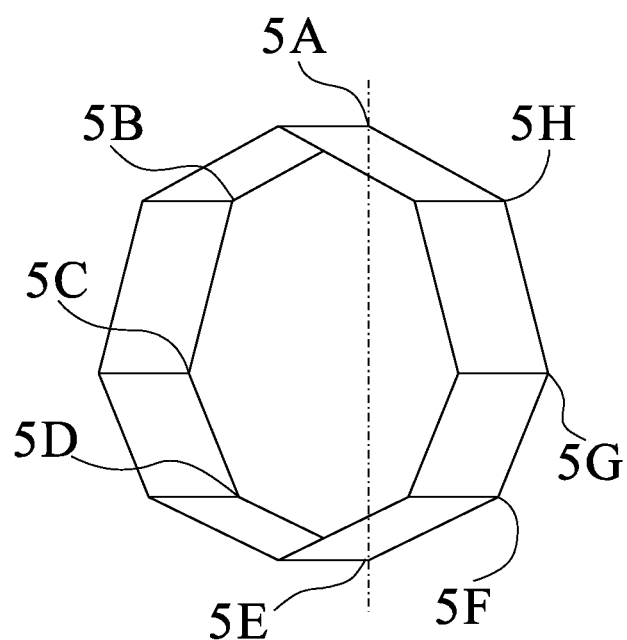
FIG. 28 shows a top plan view of the annular members of FIG. 27.
Figure 29:
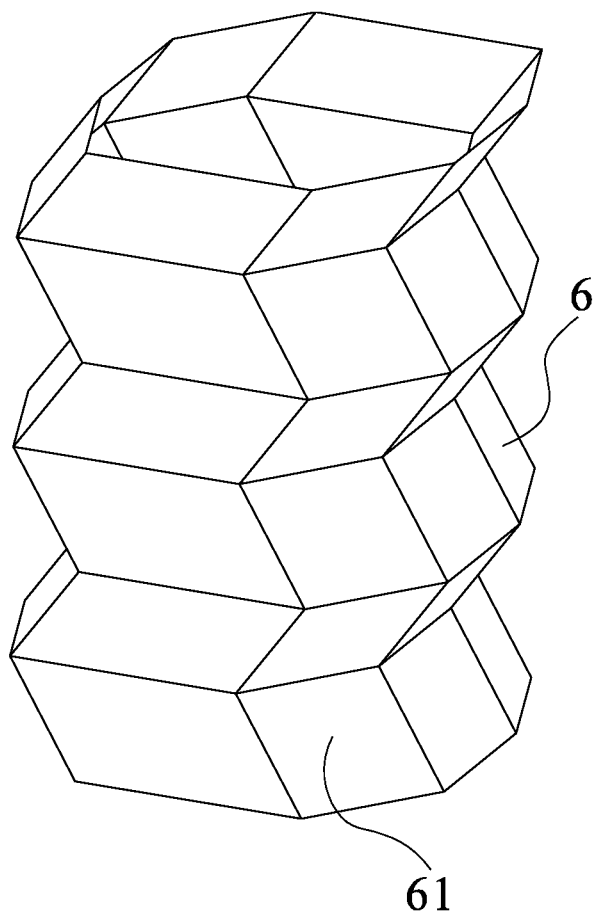
FIG. 29 shows a sixth embodiment of a foldable tubular element with one rigid degree of freedom according to the invention, illustrating a foldable tubular element being expanded and composed of an octagonal prism single layered unit in which an intersection line between two adjacent layers forms a rotationally symmetric octagon with a symmetric point located on the intersection between orthogonal lines of the octagon.
Figure 30:
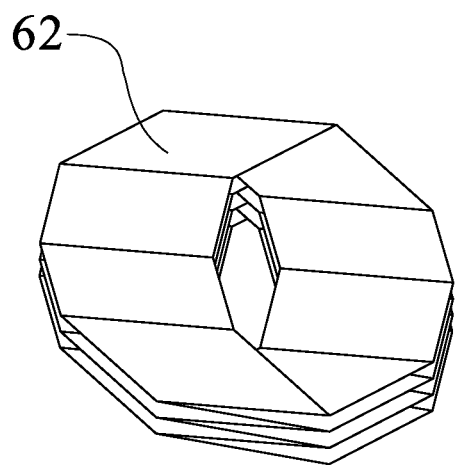
FIG. 30 shows a fully folded foldable tubular element of FIG. 29.

FIGS. 25, 26, 27 and 28 respectively show a foldable tubular element 5 in an expanded status 51 and composed of a single layered octagon prism, in a fully folded status 52, an annular structure 53 defining the structure 5, and a top plan view of the annular structure 53. As shown in FIG. 27, the intersection lines between two adjacent octagon prisms are an octagon 5A5B5C5D5E5F5G5H with a symmetric axis expanding across the apexes 5A and 5E as shown in FIG. 28. Similar to the aforementioned structure, the structure 5 is also capable of being fully expanded, concavely or convexly folded. The eight ridge lines of each octagon prism are parallel to each other. That is, the ridge lines 5A1, 5B3, 5C1, 5D3, 5E1, 5F3, 5G3, 5H3 are parallel to each other. In the same manner as the structure with a symmetric axis cross section discussed above, the first and final ridge lines of the structure 51 are located in a same plane perpendicular to the symmetric axis 5A5E of the intersection lines of adjacent octagons. Functionally, the structure 5 is also capable of being fully expanded, concavely or convexly folded.

Figure 31:
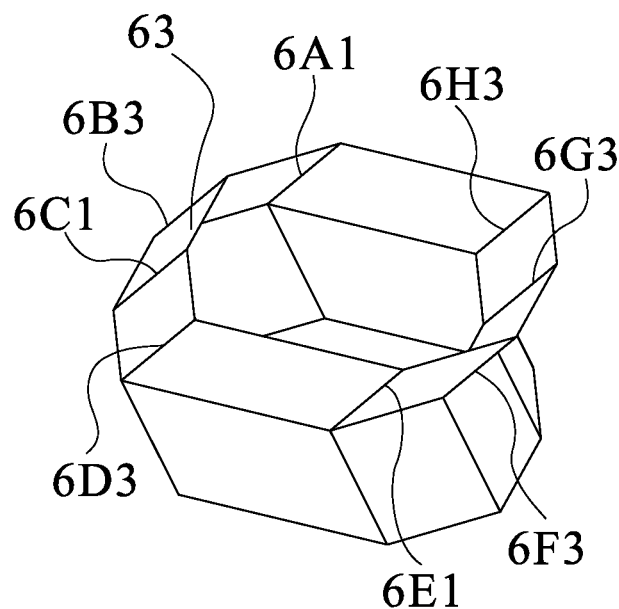
FIG. 31 shows structure of two adjacent layered annular members forming the foldable tubular element of FIG. 29.
Figure 32:
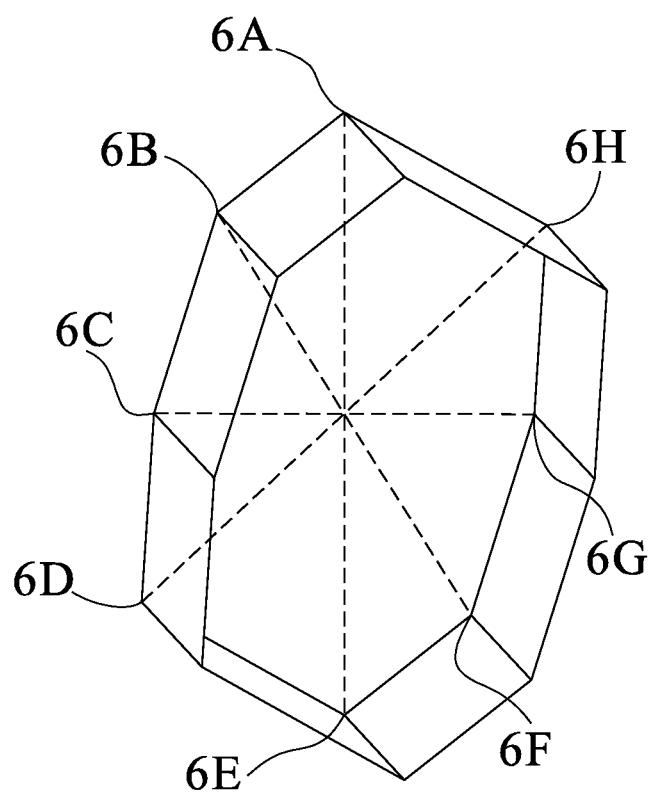
FIG. 32 shows a top plan view of the annular members of FIG. 31.

FIGS. 29, 30, 31 and 32 respectively show a foldable tubular element 6 in an expanded status 61 and composed of a single layered octagon prism, in a fully folded status 62, an annular structure 63 defining the structure 6, and a top plan view of the annular structure 63. The same as the structure 5, the structure 6 also has expanding and folding function. The ridge lines 6A1, 6B3, 6C1, 6D3, 6E1, 6F3, 6G3, 6H3 are parallel to each other. Different from structure 5, as shown in FIGS. 31 and 32, the intersection lines 6A6B6C6D6E6F6G6H of two adjacent octagon prisms of the structure 6 are rotationally symmetric lines. The symmetric center is the intersection point of the diagonals 6A6E, 6B6F, 6C6G and 6D6H. Functionally, the structure 6 is also capable of being fully expanded, concavely or convexly folded.

Based on the foldable tubular element constructed of single layered quadrangular, hexagonal and octagonal prisms respectively, a conclusion can be drawn that a foldable tubular element may also be made by single layered prisms having an even number of ridge lines and may also require having corresponding expanding and folding function when the ridge lines meet in a single layer and be parallel condition, and adjacent prisms are in a same plane condition. When the intersection lines between two adjacent prisms with an even number of ridge lines have at least one diagonal symmetric axis, the same plane of the first and final connected ridge lines of each group should perpendicular to one diagonal symmetric axis.

The construction of a foldable tubular element is explained through specific embodiments of a bent tubular element made of quadrangular prisms as shown in FIGS. 33 to 37 and in FIGS. 54 to 59. The construction of the bent tubular element also applies to that of the bent tubular element made of single layered hexagonal, octagonal prisms or prisms having even number of ridge lines.

The construction of a foldable tubular element is explained through specific embodiments of a tubular element made of pentagonal, hexagonal, heptagonal and octagonal prisms as shown in FIGS. 38 to 53. The construction of the tubular element also applies to that of the tubular element made of single layered pentagonal, hexagonal, heptagonal and octagonal prisms or prisms having any number greater than 3 of ridge lines.

Figure 33:
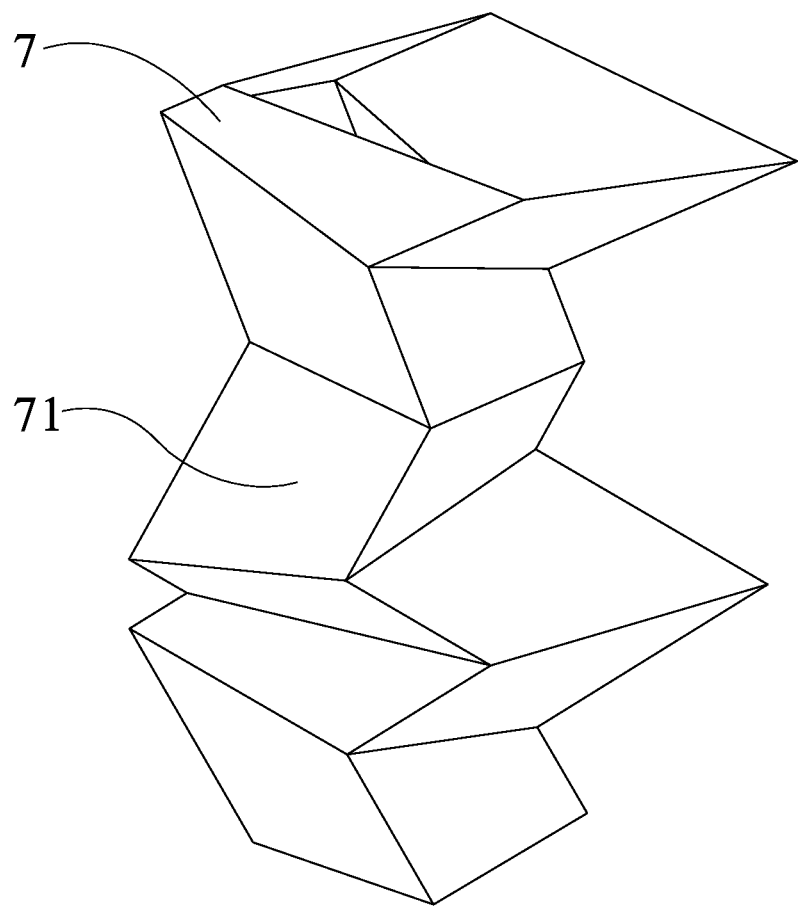
FIG. 33 shows a seventh embodiment of a foldable tubular element with one rigid degree of freedom according to the invention, illustrating a foldable tubular element being expanded and composed of a plurality of single layered units with the same corresponding angle.
Figure 34:
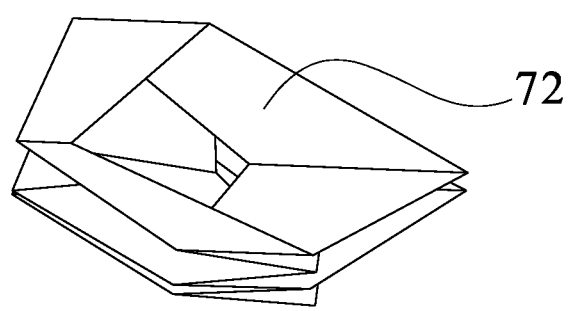
FIG. 34 shows a fully folded foldable tubular element of FIG. 33.
Figure 35:
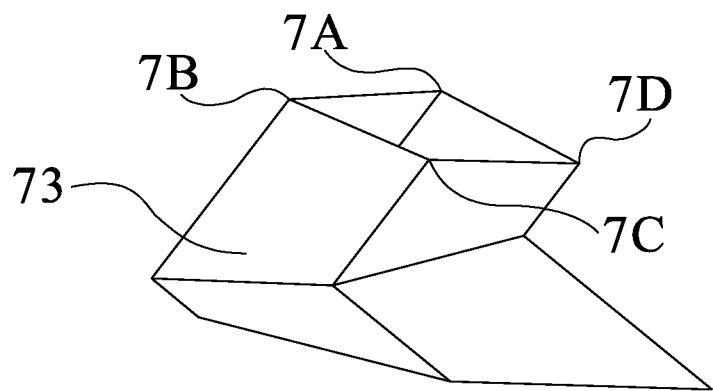
FIG. 35 illustrates an initial period for constructing the structure of FIG. 33, showing that an annular member is formed by two single layered units having the same angle and functions as the base of the structure of FIG. 33.
Figure 36:
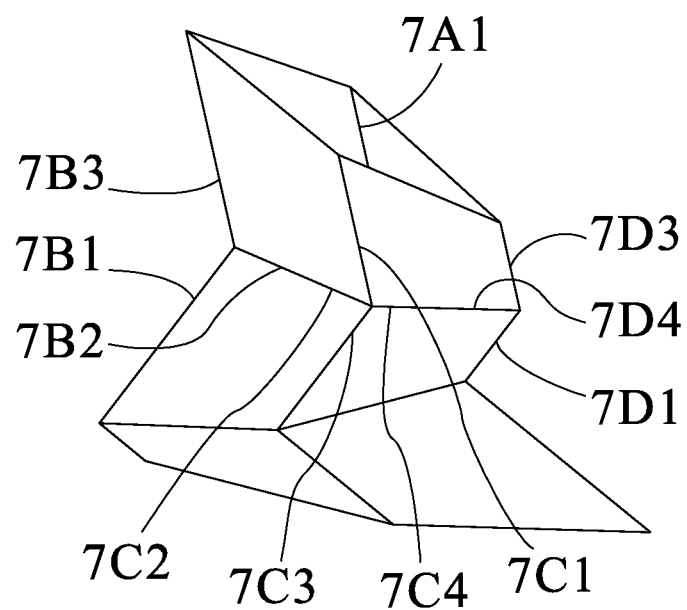
FIG. 36 shows addition of a new single layered unit onto the structure of FIG. 35.
Figure 37:
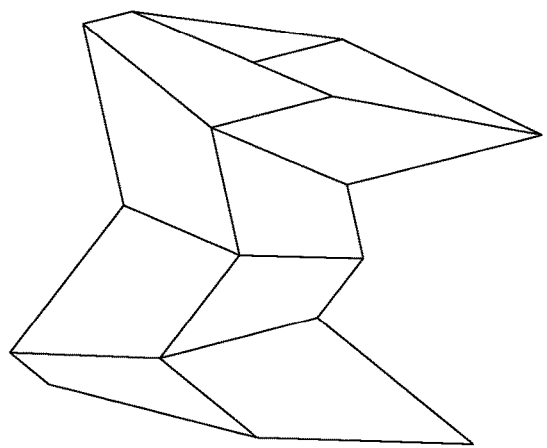
FIG. 37 shows addition of a new single layered unit onto the structure of FIG. 36.

FIGS. 33 and 34 respectively show an expanded status 71 and fully folded status 72 of a foldable bent tubular element 7 made of single layered units with the same intersection line angle. Number 73 represents an annular structure forming the present structure. FIGS. 35, 36 and 37 show a course of forming the structure 7 in sequence. From top to bottom, a new layer is added gradually. The single layered unit of the bent tubular element 7 is formed by four planar trapezoids which are connected one another to define an annular structure. Each single layer of the structure 7 is formed based on a previous single layer and may not be identical to other single layers. Construction of a single layer follows the rules below: 1) The angle of intersection lines of thus constructed single layer is identical to that of a previous single layer. For example, as shown in FIG. 36, 7B23=7B12, 7C12=7C23, 7C41=7C34, 7D34=7D41. As the ridge lines 7A3 (not shown), 7B1, 7C3 and 7D1 of the previous single layer are parallel to each other, the ridge lines 7A1, 7B3, 7C1 and 7D3 of the current single layer are also parallel to each other. 7B2 and 7D4 are intersection lines of an intersection plane of two adjacent prisms. 2) The intersection lines between the previous and current single layers are always a line-symmetric or rotational symmetric planar polygon with even number of sides. As shown in FIG. 35, a cross section 7A7B7C7D is a line-symmetric quadrangular. 3) when constructing a single layer, it should be met that the ridge lines should be located in a same plane with the ridge lines connected thereto of the previous single layer. When the intersection lines of two adjacent single layers form a polygon of even number of sides with at least one diagonal symmetric axis, these planes should be perpendicular to one diagonal symmetric axis.

Figure 38:
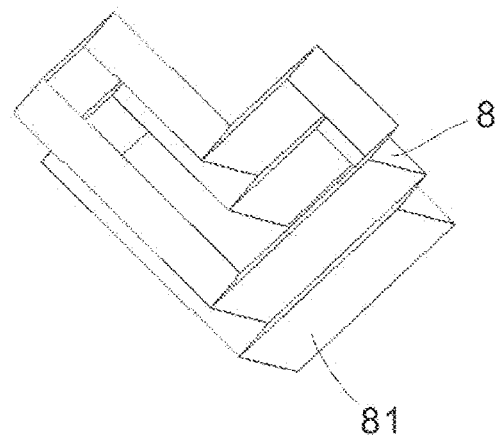
FIG. 38 shows an eighth embodiment of a foldable tubular element with one rigid degree of freedom according to the invention, and it also shows the element constructed of a hexagonal prism single layer and in an expanded state, and in this structure, the intersection lines between two adjacent layers are an asymmetrical concave hexagon formed by removing a common portion of a combined symmetrical quadrangular and a parallelogram.
Figure 39:
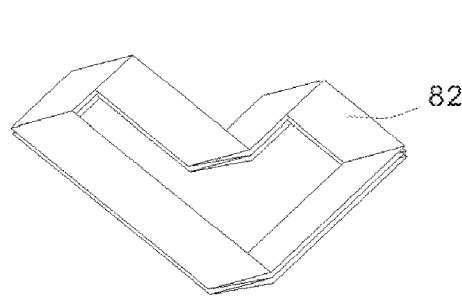
FIG. 39 shows a fully folded foldable tubular element of FIG. 38.
Figure 40:
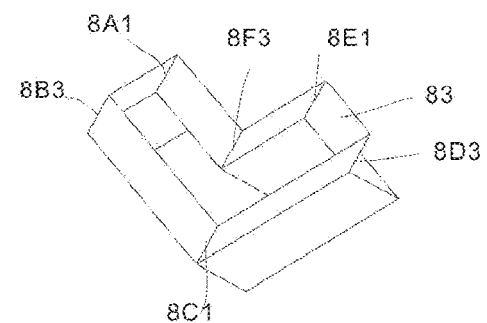
FIG. 40 shows the structure of two adjacent layered annular members forming the foldable tubular element of FIG. 38.
Figure 41:
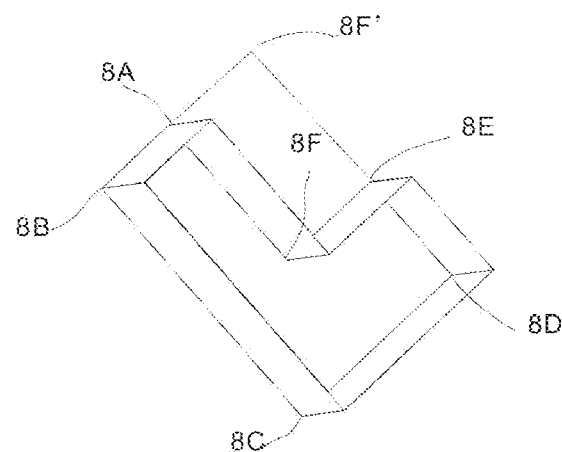
FIG. 41 shows a top plan view of the annular members of FIG. 38.

FIG. 38 shows the foldable tubular construction 8 constructed of hexagon single layers and shown in an expanded state 81. FIGS. 39, 40 and 41 show respectively a completely folded state 82, annular construction 83 forming the construction 8, and top plane view of the annular construction 83. The intersection lines of the adjacent hexagonal prisms which form the annular construction 83 are an asymmetrical concave hexagon 8A8B8C8D8E8F defined by removal of a common part from the combination of the rotational symmetrical quadrangle 8F'8B8C8D and a parallelogram 8F'8A8F8E. In addition, ridge lines of each hexagonal prism of the annular construction 83 are parallel with each other. In other words, ridge lines 8A1, 8B3, 8C1, 8D3, 8E1 and 8F3 are parallel to each other. Moreover, in case that the intersection lines of the adjacent hexagonal prisms are an asymmetrical concave hexagon defined by removal of a common part from the combination of the line-symmetric quadrangle and parallelogram, it also is of one kind of construction 8.

Figure 42:
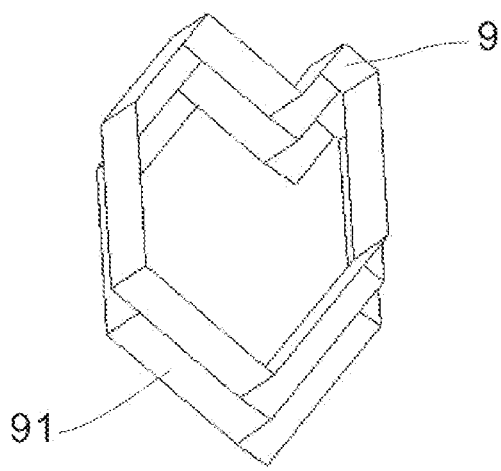
FIG. 42 shows a ninth embodiment of a foldable tubular element with one rigid degree of freedom according to the invention, and it also shows the element constructed of an octagonal prism single layer and in an expanded state, and in this structure, the intersection lines between two adjacent layers are an asymmetrical concave octagon formed by removing a common portion of a combined symmetrical quadrangular and a parallelogram.
Figure 43:
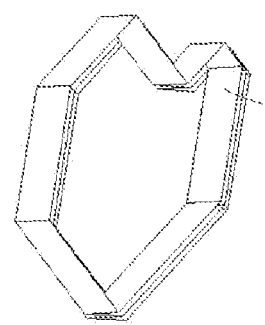
FIG. 43 shows a fully folded foldable tubular element of FIG. 42.
Figure 44:
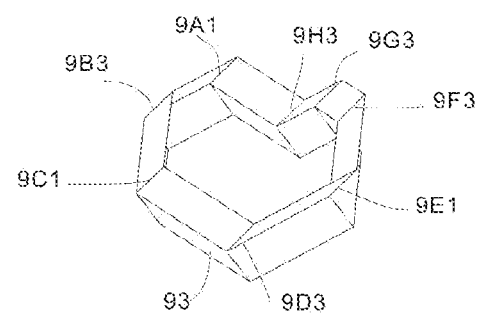
FIG. 44 shows structure of two adjacent layered annular members forming the foldable tubular element of FIG. 42.
Figure 45:
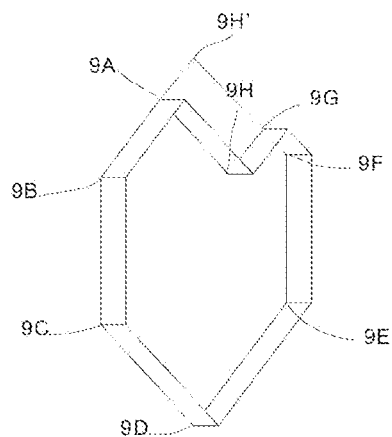
FIG. 45 shows a top plan view of the annular members of FIG. 42

FIG. 42 shows the foldable tubular construction 9 constructed of octagonal prism single layers and shown in an expanded state 91. FIGS. 43, 44 and 45 show respectively a completely folded state 92, annular construction 93 forming the construction 9, and top plane view of the annular construction 93. The intersection lines of the adjacent hexagonal prisms which form the annular construction 93 are an asymmetrical concave octagon 9A9B9C9D9E9F9G9H defined by removal of a common part from the combination of the rotationally symmetric hexagon 9H'9B9C9D9E9F and a parallelogram 9F'9A9H9G. In addition, ridge lines of each octagonal prism of the annular construction 93 are parallel with each other. In other words, ridge lines 9A1, 9B3,9C1,9D3,9E1,9F3,9G3 and 9H3 are parallel to each other. Moreover, in case that the intersection lines of the adjacent octagonal prisms are an asymmetrical concave octagon defied by removal of a common part from the combination of the line-symmetric hexagon and parallelogram, it also is of one kind of construction 9.

Figure 46:
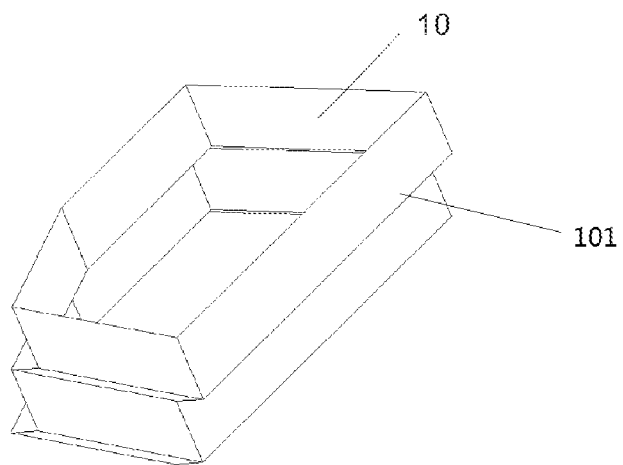
FIG. 46 shows a tenth embodiment of a foldable tubular element with one rigid degree of freedom according to the invention, and it also shows the element constructed of a pentagonal prism single layer and in an expanded state, and in this structure, the intersection lines between two adjacent layers are an asymmetrical pentagon formed by removing a common portion of a combined line-symmetric quadrangular and a parallelogram.

FIG. 46 shows the foldable tubular construction 10 constructed of pentagonal prism single layers and shown in an expanded state 101. FIGS. 47, 48 and 49 show respectively a completely folded state 102, annular construction 103 forming the construction 10, and top plane view of the annular construction 103. The intersection lines of the adjacent pentagonal prism which form the annular construction 103 are an asymmetrical concave pentagon 10A10B10C10D10E defined by removal of a common part from the combination of the linearly symmetrical quadrangle 10E'10C10D10E and a parallelogram 10A10B10C10E'. In addition, ridge lines of each pentagonal prism of the annular construction 103 are parallel with each other. In other words, ridge lines 10A1,10B3,10C1,10D3 and 10E3 are parallel to each other.

Figure 50:
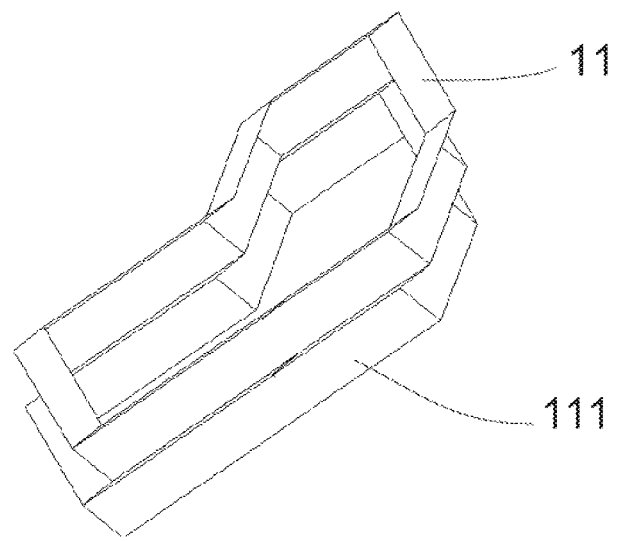
FIG. 50 shows an eleventh embodiment of a foldable tubular element with one rigid degree of freedom according to the invention, and it also shows the element constructed of a seven-sided prism single layer and in an expanded state, and in this structure, the intersection lines between two adjacent layers are an asymmetrical polygon with seven sides formed by removing a common portion of a combined symmetrical hexagon and a parallelogram.
Figure 51:
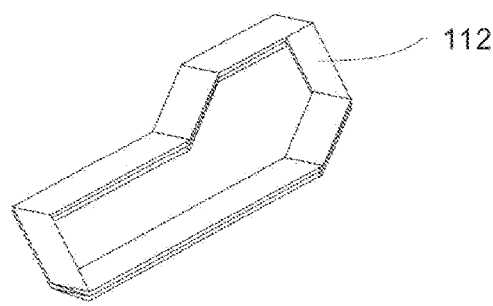
FIG. 51 shows a fully folded foldable tubular element of FIG. 50.
Figure 52:
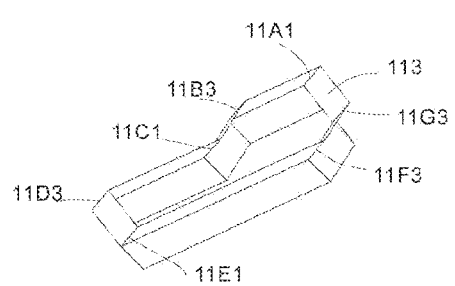
FIG. 52 shows structure of two adjacent layered annular members forming the foldable tubular element of FIG. 50.
Figure 53:
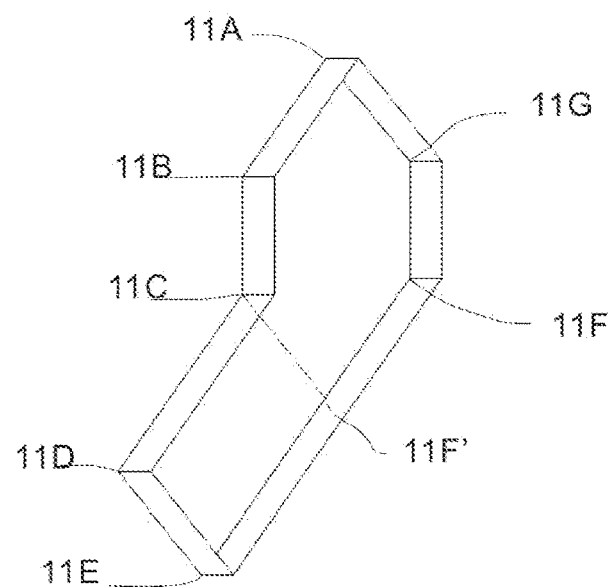
FIG. 53 shows a top plan view of the annular members of FIG. 50.
Figure 54:
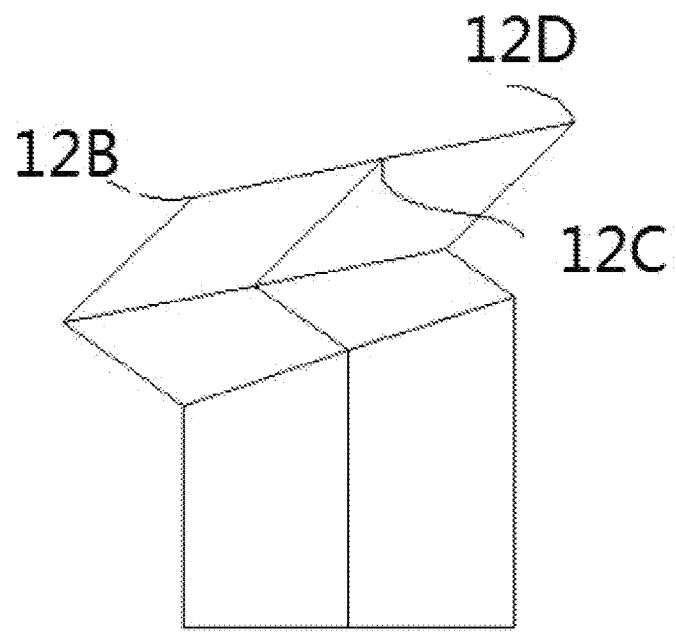
FIG. 54 shows a twelfth embodiment of a foldable tubular element with one rigid degree of freedom according to the invention, and it also shows the foldable tubular element in a front elevation and constructed of any single layered unit.
Figure 55:
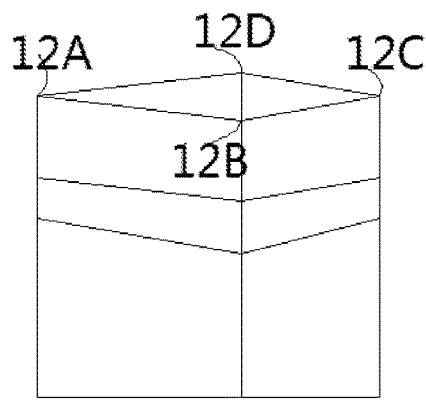
FIG. 55 shows a left view of the foldable tubular element constructed of any single layered unit of FIG. 54.

FIG. 50 shows the foldable tubular construction 11 constructed of heptagonal prism single layers and shown in an expanded state 111. FIGS. 51, 52 and 53 show respectively a completely folded state 112, annular construction 113 forming the construction 9, and top plane view of the annular construction 113. The intersection lines of the adjacent heptagonal prisms which form the annular construction 113 are an asymmetrical concave heptagon 11A11B11C11D11E11F11G defined by removal of a common part from the combination of the rotationally symmetric hexagon 11A11B11C11F'11F11G and a parallelogram 11C11D11E11F'. In addition, ridge lines of each heptagonal prism of the annular construction 113 are parallel with each other. In other words, ridge lines 11A1,11B3,11C1,11D3, 11E1,11F3 and 11G3 are parallel to each other. Moreover, in case that the intersection lines of the adjacent heptagonal prisms are an asymmetrical concave heptagon defied by removal of a common part from the combination of the line-symmetric hexagon and parallelogram, it also is of one kind of construction 11.

Figure 56:
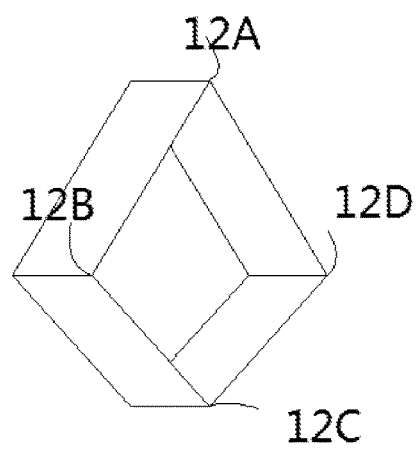
FIG. 56 shows a top view of the foldable tubular element constructed of any single layered unit of FIG. 54.
Figure 57:
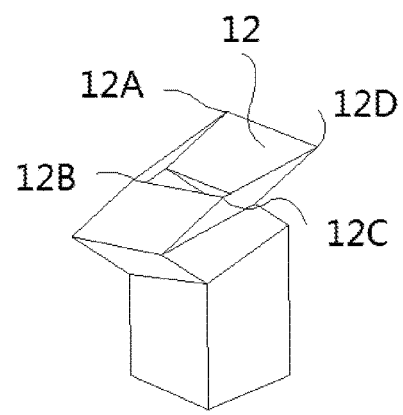
FIG. 57 shows a structural view of the foldable tubular element constructed of any single layered unit of FIG. 54.

FIGS. 54, 55, 56 and 57 respectively show a front, left, top plan, and perspective views of a foldable bent tubular element 12 made of any single layer unit. The structure 12 is also made by addition of a single layer in sequence. The structure thus made should satisfy the following conditions: 1) The intersection lines between the previous and current single layer units are planar polygon with N sides. As shown in FIG. 56, a quadrilateral facets 12A12B12C12D. 2) The ridge lines of each single layer unit should be parallel to each other. 3) when the intersection lines of two adjacent single layers are a polygon of N sides with at least one diagonal symmetric axis, the first and final ridge lines of each group of the tubular element should be located in a same plane, and be perpendicular to one diagonal symmetric axis, and reference is made to aforementioned constructions 1, 3 and 5. The angle between intersection lines of each single layer of the structure 12 may not be identical to that of two adjacent layers. As such, it can be understood that the structure 12 may not be in a fully folded status where adjacent planar units contact with each other. Normally, only the single layer having smallest foldable range may be fully folded or expanded. Compared to bent tubular element 7, the structure 12 is less limited. Accordingly, the structure 12 represents a most common situation of the foldable bent tubular element.

Figure 58:
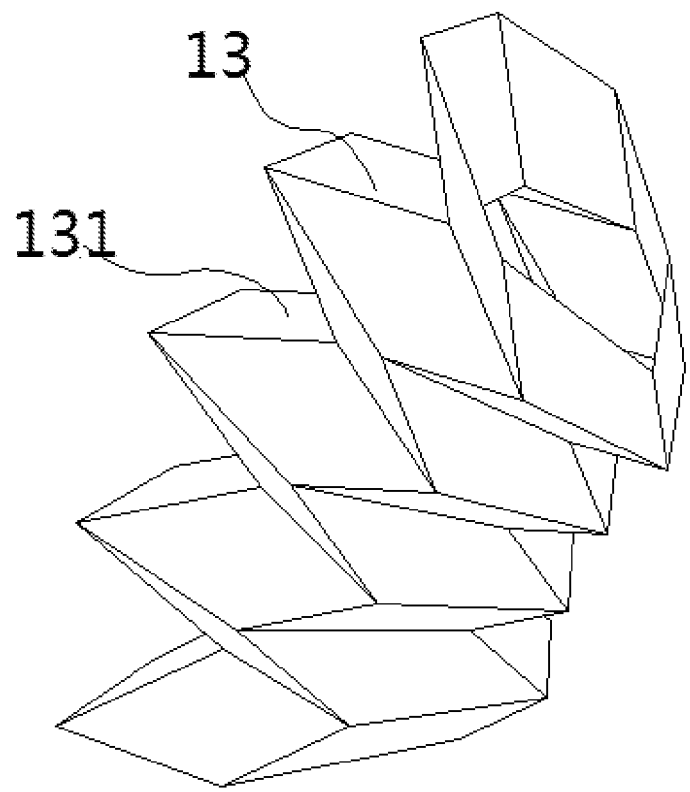
FIG. 58 shows a thirteenth embodiment of a foldable tubular element with one rigid degree of freedom according to the invention, and it also shows the foldable tubular element constructed of a hexagonal prism single layer and in an expanded state.
Figure 59:
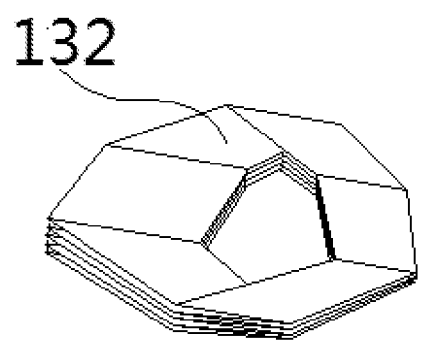
FIG. 59 shows a fully folded foldable tubular element of FIG. 58.

FIGS. 58 and 59 show a bent tubular element 13 in expanded status 131 and fully folded status 132. Said bent tubular element 13 is made according to the foregoing bent tubular element construction method.

It is noted that: 1) when all the planar quadrangular of the structure are of a parallelogram, the so constructed tubular element made of single layered prism with N ridge lines is an expandable and foldable straight tubular element such as the structures 1, 2, 3, 4, 5, 6,8,9,10 and 11; 2) when partial or all planar quadrangular of the structure are of trapezoid, so constructed tubular element made of single layered prism with N ridge lines is an expandable and foldable bent tubular element such as the structures 7, 12 and 13. In other words, the straight tubular structure is a specific example of bent tubular structure, and both fall within the scope of the invention.

Though various embodiments of the invention have been illustrated above, the description and the drawings are not the limitation to the invention. A person of ordinary skill in the art will understand that, variations and improvements made upon the illustrative embodiments fall within the scope of the invention, and the scope of the invention is only limited by the accompanying claims and their equivalents.

What is claimed is:

1. A foldable tubular construction with one rigid degree of freedom, comprising a plurality of layered tubular units each with an enclosing side wall, a head rim and tail rim, said enclosing side wall being formed by N side faces, said head rim and said tail rim each defining an N-sided polygon, said side faces each being a rigid planar quadrilateral with two opposing sides forming two side joining lines with corresponding sides of two adjacent faces of a same tubular unit and another side forming a base joining line with a corresponding side of an adjacent face of a different tubular unit, said plurality of layered tubular units being joined sequentially wherein a head-to-head connection is formed between the head rim of a tubular unit and the head rim of a preceding adjacent tubular unit and/or a tail-to-tail connection is formed between the tail rim of said tubular unit and the tail rim of a following adjacent tubular unit; each of said tubular unit has exactly N side joining lines, all parallel to each other; said head-to-head connection or tail-to-tail connection consists of N base joining lines interconnected to form an N-sided polygon within a same plane; two side joining lines and two base joining lines join at one end to form an apex; exactly N apexes are formed in each head-to-head connection or tail-to-tail connection; and N is a number greater than 3, wherein the N-sided polygon is non-rotational symmetric, wherein said foldable tubular construction is interchangeable between a folded state and an extended state by varying the angle between said side joining lines and the plane defined by said base joining lines, with said angle being greater in said extended state than in said folded state, and wherein said N-sided polygon defined by said head rim is of the same size and shape as that defined by said tail rim.

2. The foldable tubular construction according to claim 1, wherein said rigid planar quadrilaterals are all parallelograms and said foldable tubular construction is extendable along a straight line.

3. The foldable tubular construction according to claim 1, wherein said rigid planar quadrilaterals are all trapezoids and said foldable tubular construction is extendable along a zig-zag line.

4. The foldable tubular construction according to claim 1, wherein some of said rigid planar quadrilaterals are trapezoids and some of said rigid planar quadrilaterals are parallelograms, and said foldable tubular construction is extendable along a zig-zag line.

* * * * *